United States Patent [19]

Girijavallabhan et al.

[11] Patent Number: 4,530,793

[45] Date of Patent: * Jul. 23, 1985

[54] PROCESSES FOR THE PRODUCTION OF PENEMS

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Madison, N.J.

[*] Notice: The portion of the term of this patent subsequent to Apr. 17, 2001 has been disclaimed.

[21] Appl. No.: 445,295

[22] Filed: Nov. 29, 1982

[51] Int. Cl.$^3$ ............... C07D 499/00; A61K 31/545
[52] U.S. Cl. ..................... 260/245.2 R; 260/239 A
[58] Field of Search ............ 260/245.2 R, 245.2 T; 424/270

[56] References Cited

U.S. PATENT DOCUMENTS

| 4,272,437 | 6/1981 | Menard et al. | 260/239 A |
| 4,282,150 | 8/1981 | Menard et al. | 424/270 |
| 4,443,373 | 4/1984 | Girijavallabhan et al. | 424/270 |

FOREIGN PATENT DOCUMENTS

| 0002210 | 6/1979 | European Pat. Off. |
| 2042520 | 9/1980 | United Kingdom . |
| 2074563A | 11/1981 | United Kingdom . |

Primary Examiner—Nicholas S. Rizzo
Attorney, Agent, or Firm—Anita W. Magatti; Gerald S. Rosen; Thomas D. Hoffman

[57] ABSTRACT

Processes for the production of 6-hydroxyethyl-2-substituted thio penem-3-carboxylates are disclosed as well as novel penems.

3 Claims, No Drawings

PROCESSES FOR THE PRODUCTION OF PENEMS

BACKGROUND

This invention relates to processes for preparing 6-hydroxyethyl-2-substituted thio-penem-3-carboxylates (referred to herein as penems) and to novel penems and intermediates produced therein.

Penems, a recent addition of the family of synthetic beta-lactams, possess potent anti-bacterial activity. They have been prepared by laborious, time consuming, multistep processes which result in low yields and are thus uneconomical.

SUMMARY OF THE INVENTION

The present invention provides novel, facile processes which are widely applicable for preparing penems and which employ novel intermediates and novel reaction steps. The process of this invention is suitable for preparing penems represented by the formula:

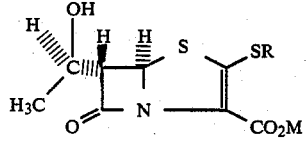

wherein R is a pharmaceutically acceptable organic radical and M is hydrogen or an alkali metal cation.

One of the process routes of this invention is a multi-step process. Nevertheless, the process is easily and economically conducted since it results in high yields and many of the intermediates produced need not be isolated. Another process route of this invention requires fewer process steps.

Novel penems produced by these processes are represented by the formula:

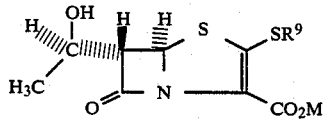

wherein $R^9$ is selected from the group consisting of

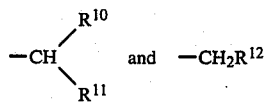

wherein $R^{10}$ is hydrogen or trifluoroloweralkyl; $R^{11}$ is trifluoroloweralkyl or dihydroxy lower alkyl; and $R^{12}$ is selected from the group consisting of 2-amino-4-thiazolyl; 5-amino-2-thiazolyl; 5-nitro-2-thiazolyl;

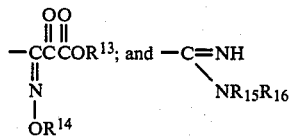

wherein $R^{15}$ and $R^{16}$ are independently hydrogen or are lower alkyl, or $R^{15}$ and $R^{16}$ together with the nitrogen to which they are attached form a cyclicamino ring of 3 to 6 members; wherein $R^{13}$ and $R^{14}$ are independently hydrogen or lower alkyl; and M is hydrogen or an alkali metal.

Compounds of formula II are useful as antibiotics, being active against both gram positive and gram negative organisms such as *Staphylococcus aureus*, *Escherichia coli* and *Pseudomnas aeruginosa*. Encompassed within the scope of this invention, is the method of eliciting an antibacterial response in a warm-blooded animal having a susceptible bacterial infection which comprises administering to said animal a non-toxic, antibacterially effective amount of a compound of formula II.

The methods of this invention are implemented using pharmaceutical compositions comprising a pharmaceutically acceptable carrier or coating and an antibacterially effective amount of a penem of formula II.

The dosage administered of the penems of this invention is dependent upon the age and weight of the animal species being treated, the mode of administration, and the type and severity of bacterial infection being prevented or reduced. Typically, the dosage administered will be in the range of 1 to 250 mg/kg, with 5 to 20 mg/kg in divided dosages being preferred.

The penems of this invention may be administered either orally or parenterally. Preferably, the compounds are administered orally.

For oral administration, the antibacterial compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, in the form of creams, or by mechanical delivery systems, e.g. transdermal.

DETAILED DESCRIPTION OF THE INVENTION

The present invention provides a process hereinafter referred to as process A, for the production of penems of the formula:

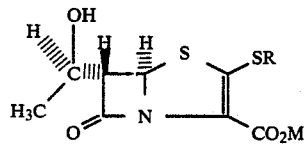

wherein R is an organic radical and M is hydrogen or an alkali metal cation; which comprises (a) reaction of an azetidinone of the formula

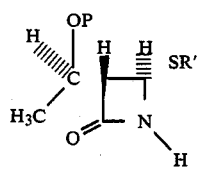

wherein P is a removable hydroxy protecting group; and $R^1$ is a sulfur protecting group selected from triphenylmethyl, 2-pyranyl, or lower alkyl carbonyl; with a compound of the formula IVa and IVb

H₂O +

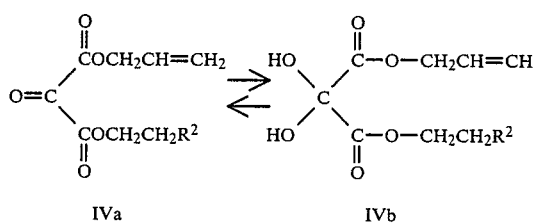

wherein R² is trimethylsilyl, t-butyldiphenylsilyl or other equivalently functioning lower alkylsilyl groups; to form the intermediate of the formula V

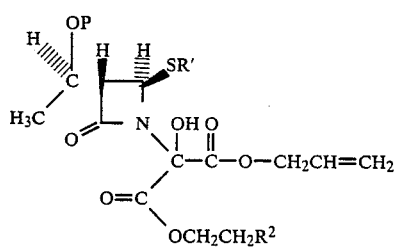

wherein P, R¹ and R² are hereinabove defined;

(b) treatment of the compound of formula V with a chlorinating agent to form the following compound of formula VI

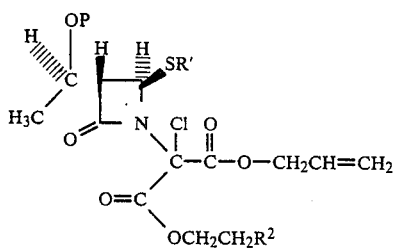

wherein P, R⁷ and R² are as defined hereinabove;

(c) treatment of the compound of formula VI with elemental zinc to effect removal of the chlorine and the removable hydroxy protecting group, and, if a removable hydroxy protecting group is utilized which is not removable with zinc, subsequent removal of said hydroxy protecting group, producing a compound of formula VII

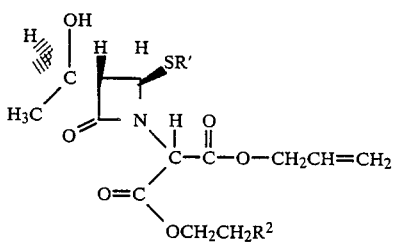

wherein R⁷ and R² are hereinabove defined;

(d) treatment of the compound of formula VII with a reactive silver, copper or mercury salt to form the compound of formula VIII

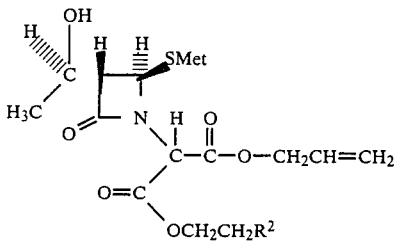

wherein R² is defined hereinabove and Met is silver, copper or mercury;

(e) treatment of the compound of formula VIII with a hydroxy protecting group to form the compound of formula IX

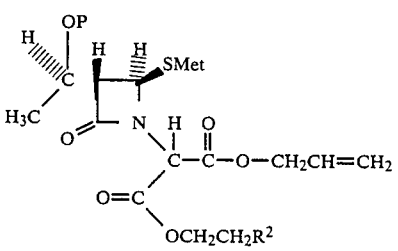

wherein R², P and Met are defined hereinabove;

(f) reaction of the compound of formula IX with a thiocarbonyl compound of formula X $$S=C(-Y)_2 \qquad (X)$$

wherein Y is a leaving group; to form a compound of formula XI

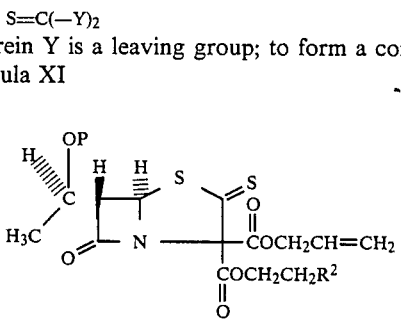

wherein P and R² are as hereinabove defined;

(g) treatment of the compound of formula XI with an aqueous acid solution to form a compound of formula XII

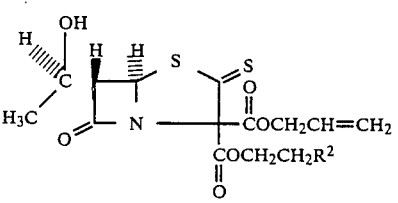

In an alternative procedure, compounds of formula XII can be prepared from compounds of formula VIII by eliminating steps (e) and (g) (i.e., the protection and subsequent deprotection of the hydroxyl group at the C-8 position).

(h) treatment of the compound of formula XII with a fluoride ion to form the compound of formula XIIIa which is tautomeric with formula XIIIb XIII(a)

XIII(b)

(i) reaction of the compound of formulas XIII(a) and XIII(b) with either a compound of the formula XIV $$RZ \quad\quad (XIV)$$

wherein R is as defined hereinabove and Z is a leaving group or with $$CF_3SO_3CH\begin{array}{c}R^{10}\\R^{11}\end{array}$$

wherein $R^{10}$ and $R^{11}$ are hereinabove defined to form a compound of formula XV

XV wherein R is defined above.

(j) treatment of a compound of formula XV under catalytic conditions to remove the allyl protecting group in the presence of an alkali base (if the product is a zwitterion, deprotection requires only the catalyst and any mild nucleophile, e.g. $H_2O$, alcohol, etc.) to form the compounds of formula I

I wherein R and M are as hereinabove defined.

The process hereinafter referred to as process B, according to this invention for preparing a compound of the formulas XIIIa and XIIIb XIII(a)

XIII(b)

which comprises steps (a) to (h) of Process A, above.

Alternatively, and preferably, the process hereinafter referred to as process C, for preparing a compound of formulas XIII(a) and XIII(b)

XIII(a)

XIII(b)

which comprises
(a) reaction of an azetidinone of the formula

XVI wherein $R^1$ is a sulfur protecting group selected from triphenylmethyl, 2-pyranyl, or lower alkyl carbonyl; with an allyl α-substituted acetate of formula XVII $$WCH_2CO_2CH_2CH=CH_2 \quad\quad XVII$$

wherein W is a leaving group; to form the intermediate of the formula XVIII

XVIII (b) treatment of the compound of formula XVIII with a reactive silver, copper or mercury salt to form the compound of formula XIX

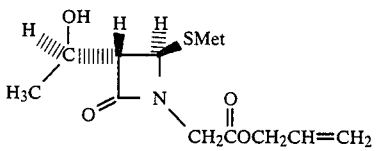

wherein Met is silver, copper or mercury.

(c) treatment of the compound of formula XIX with a hydroxy protecting group to form the compound of formula XX

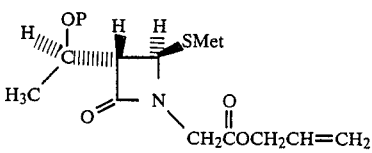

wherein P and Met are as hereinabove defined;

(d) reaction of the compound of formula XX with a thiocarbonyl compound of formula X

wherein Y is a leaving group to form a compound of formula XXI

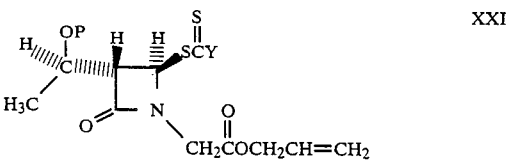

wherein Y and P are as hereinabove defined;

(e) treatment of compound XXI with a nonnucleophilic strong base to form a compound of formula XXII(a) which is tautomeric with formula XXII(b)

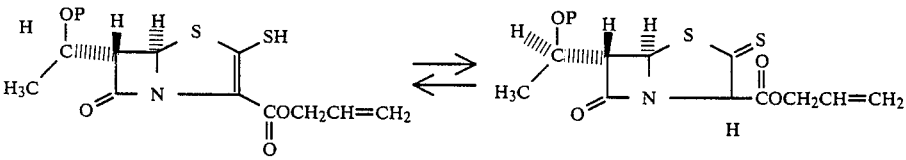

wherein P is as hereinabove defined;

(f) treatment of the compounds of formulas XXII(a) and XXII(b) under conditions which effect removal of the hydroxy protecting group to form the compounds of formula XIII(a) and XIII(b).

Optionally, alkylation of the intermediate of formulas XXII(a) and XXII(b) can be performed in situ in step (e), thereby directly obtaining the defined penem of formulas XIII(a) and XIII(b).

Unless otherwise stated, the term "loweralkyl" includes branched- and straight-chain alkyl groups of from 1 to 4 carbons and includes, for instance, methyl, ethyl, n-propyl, isopropyl, t-butyl and the like.

The term "fluoro loweralkyl" includes branched- and straight-chain loweralkyl alkyl groups substituted with 1 to 6 fluoro groups.

The term "organic radical" includes the groups lower alkyl; loweralkyl substituted with one or more substituents independently selected from halogen, hydroxy, lower alkoxy, cyano, oxo, carb(lower)alkoxy, carbamoyl, amino, lower alkyl amino, dilower alkyl amino, lower alkanoylamino, alkylthio, arylthio, heterocyclicthio,

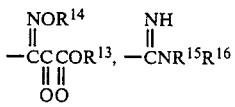

(wherein $R^{14}$ and $R^{13}$ are independently hydrogen or lower alkyl and $R^{15}$ and $R^{16}$ are each lower alkyl or $R^{15}$ and $R^{16}$ together with the nitrogen to which they are attached form a cyclicamino ring of 3 to 6 members) butanolidyl, aryl, heteroaryl or aryl or heteroaryl substituted with 1 to 4 substituents independently selected from lower alkyl, hydroxy, lower alkoxy, halogen, halo lower alkyl, lower alkylthio, amino, lower alkyl amino, dilower alkyl amino, carboxy lower alkyl, nitro, and cyano;

Aryl or aryl substituted with 1 to 4 substituents independently selected from lower alkyl, hydroxy, lower alkoxy halogen, halo lower alkyl, lower alkylthio, amino, lower alkyl amino, dilower alkyl amino, carboxy lower alkyl, nitro and cyano;

Heteroaryl or heteroaryl substituted with 1 to 4 substituents independently selected from lower alkyl, hydroxy lower alkoxy, halogen, halo lower alkyl, lower alkylthio, lower alkyl sulfonyl, amino, lower alkyl amino, dilower alkylamino, carboxy lower alkyl, nitro and cyano.

The term "halogen" means fluoro, chloro and bromo.
The term "loweralkanoylamino" means the group

wherein $R^{17}$ is lower alkyl.

The term "aryl" means aromatic groups of 6 to 10 carbons and includes phenyl, napthyl and the like.

The term "heterocyclic" means cyclic groups of 5 or 6 ring atoms wherein 1 to 4 ring atoms are selected from the group consisting of nitrogen, sulfur and oxygen and includes for instance piperidyl, piperizinyl, pyrrolidinyl, thiazolidinyl, thiomorpholinyl, morpholinyl, tetrahydrofuranyl, tetrahydropyranyl, tetrahydrothiofuranyl, and tetrahydrothiopyranyl. Also included are the positional isomers of the above, e.g. 3-piperidinyl and 4-piperidinyl, 2-pyrrolidinyl and 3-pyrrolidinyl.

The term "heteroaryl" means aromatic heterocyclic groups of 5 to 10 ring atoms wherein 1 to 3 ring atoms are selected from the group consisting of nitrogen, sulfur and oxygen and includes for instance imidazoyl, pyridinyl, pyrimidinyl, thiazolyl, pyrrolyl, pyrazolyl, pyrazinyl, furyl, thiofuryl, triazolyl, oxazolyl, 1,2,3- oxadiazole, indolyl, benzothiofuranyl, tetrazolyl and the like.

The term "alkali metal" means sodium and potassium salts.

The term "removable hydroxy protecting group" means any such group conventionally used for this purpose, with the only requirement being compatability with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethyltributylsilyl, trimethylsilyloxycarbonyl and trimethylsilyl.

The preferred stereochemistry of the reactants and the intermediates in the above processes is as indicated in the various formulas, i.e. (5R,6S,8R). However, it is to be understood, that the process of this invention is operative for other stereoisomers and involves the selection of the starting material of the desired stereochemical configuration.

In a highly preferred embodiment of processes A and B of the present invention, the intermediates formed in each reaction step are not isolated but remain in the reaction vessel and are treated according to the next reaction step. This facilitates the process to a very great extent, since several steps can be carried out in the same solvent, without regard to separation of the desired product.

For instance, in a preferred embodiment of process A the mixed ester of formula IV is added to the intermediate of formula III to form the hydroxy intermediate of formula V. This intermediate of formula V is then directly treated with the chlorinating agent, preferably thionyl chloride, to form the chloride intermediate of formula VI. This intermediate, again without isolation, is treated directly with elemental zinc to concommitantly remove the hydroxy protecting group on the 6-substituent and the chlorine atom so as to afford the intermediate of formula VII. Thus steps (a), (b) and (c) of either of the aforementioned processes are conducted in the same reaction vessel, in the same solvent, and without any wastage caused by isolation of the intermediate compounds.

Again, in a preferred embodiment, the intermediate of formula VIII is utilized directly in steps (e) and (f) without isolation. Thus, steps (d), (e) (f) and (g) are conducted sequentially.

It is likewise preferred to dispense with the isolation of the intermediate of formulas XIII(a) and XIII(b) when preparing compounds of formula I. Thus steps (h), (i) and (j) may be conducted sequentially.

The first step (a) of processes A and B of this invention wherein an azetidinone of formula III is reacted with a compound of formulas IV(a) and IV(b) to form the intermediate of formula V is typically conducted in a suitable organic solvent at about room temperature. Preferably, the organic solvent is a polar organic solvent, such as dimethylformamide, but other suitable solvents such as tetrahydrofuran, acetonitrile and dimethylsulfoxide may also be used. The compounds of formulas IV(a) and IV(b) are mixed diesters and their hydrated forms. They are represented by the following formulas IV(a) and IV(b)

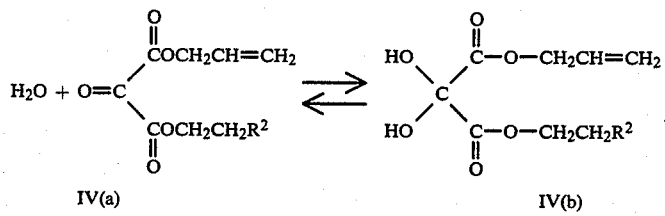

wherein $R^2$ is trimethylsilyl, t-butyldiphenylsilyl or other equivalently functioning lower alkylsilyl group. Preferred are the trimethylsilyl and t-butyldiphenylsilyl groups, with trimethylsilyl being most preferred due to its ready availability and ease of use.

Step (b) of these processes wherein the compound of formula V is chlorinated to form the compound of formula VI is typically conducted in a suitable organic solvent at temperatures of about $-15°$ C. to $10°$ C. in the presence of an acid acceptor. Where the solvent utilized is also an acid acceptor, for instance, pyridine, no additional reagent is utilized. Alternatively, an organic solvent such as methylene chloride, chloroform, dimethyl formamide or acetonitrile may be utilized. In these cases, a separate acid acceptor, organic or inorganic must be added to the reaction mixture. Typical of the suitable acid acceptors are organic bases such as pyridine or triethylamine and inorganic bases such as sodium or potassium carbonate. As mentioned hereinabove, the chlorinating reaction may be carried out directly on the product of step (a) without isolation of the product. When this is the case, the solvent utilized is necessarily identical to that utilized in step (a). The chlorinating agent itself may be any of a variety utilized for the conversion of alcohols to chlorides such as thionyl chloride, oxalyl chloride, phosphorus pentachloride, phosphorus trichloride or phosphorus oxychloride. Of these, thionyl chloride is most preferred.

Step (c) of these processes wherein the chlorinated intermediate of formula VI is dechlorinated and the hydroxy group of the 6-substituted concommitantly deprotected to form the intermediate of formula VII may likewise be conducted in the same solvent utilized for steps (a) and (b). Howerver, any suitable organic solvent can be utilized, for instance, tetrahydrofuran, methylene chloride or dimethylformamide. Water, or any proton source, adjusted by the addition of a mild acid, can be added to enhance the activity of zinc. Typical temperatures range from $-15°$ C. to about room temperatures (about $25°$ C.) with a temperature of about $0°$ C. being particularly preferred. Most preferably, the removable hydroxy protecting group utilized is one which is removable by elemental zinc. However, in the event that a removable hydroxy protecting group is utilized which is not so removable (by the zinc), a separate removal step is simply conducted to remove the hydroxy protecting group. This separate removal step may occur immediately after step (c) of the instant process, or at any other time after step (c) convenient to the conduct of the process. Such removal steps are well-known in the $\beta$-lactam art.

Step (d) of these processes involves the conversion of the compound of formula VII to the compound VIII. Typically, a polar solvent such as methanol, ethanol, dimethylformide, tetrahydrofuran or water is utilized for this reaction. Metal sals, e.g. those of silver, mercury or copper can be utilized in this step and may be any reactive salt of the metal in which the anion does not interfere in the reaction. Silver salts are preferred and include organic and inorganic salts such as silver nitrate, silver fluoborate and silver acetate, and the like with silver nitrate being most preferred. Typical suitable copper salts are those such as copper (II) acetate and copper (II) nitrate. Typical suitable mercury salts are those such as mercuric acetate. Lead salts may also be utilized although the reaction will be much slower. Silver salts are most preferred due to their ease of recovery and relative nontoxicity. The use of an acid acceptor, e.g., pyridine or triethylamine, facilitates the reaction of this step. The reaction preferably takes place under an inert atmosphere with a nitrogen atomosphere preferred.

Step (e) of these processes involves the protection of the 6-hydroxy substituent. Optionally, if during step (c) the 6-hydroxy protecting group was not removed, this step may be eliminated. Hydroxy protecting groups are well known in the beta-lactams art. A particularly preferred reagent for this step is bis silylacetamide which readily forms the trimethylsilyl protecting group at the 6-hydroxy moiety. Preferably step (e) is conducted directly upon the completion of step (d) without isolation of the metal salt intermediate of formula VIII. Thus the inert solvent utilized, e.g. DMF, may be the same as the one used in step (d). Solvents such as chloroform, methylene chloride and the like may also be employed in step (e). Temperatures for the reaction of step (e) range from 0° C. to 30° C.

Step (f) of the process is wherein the metal salt of formula VIII is converted to the thiocarbonyl compound of formula XI by reaction of the compound of formula VIII with the thiocarbonyl reagent of formula X. Typically, this step (f) is conducted directly upon the completion of step (e) without isolation of the metal salt intermediate of formula VIII. Thus, the solvent utilized may be the same as the one used in step (e). Temperatures for the reaction of step (e) range from about 10° C.–45° C., with room temperature (about 25° C.) being generally preferred. The thiocarbonyl reagent of formula X has the following structure $$S=C(-Y)_2 \quad (X)$$

wherein Y is a leaving group. Typical of such leaving groups are chloro, bromo, iodo or imidazolyl. For the purposes of the processes of this invention, 1,1'-thiocarbonyldiimidazole is preferred due to its crystalline nature and ease of use.

Step (g) of these processes involves the removal of the 6-hydroxy protecting group to form the compound of formula XII. Methods for the removal of this group are well known in the β-Lactam art. Preferably, when the 6-hydroxy protecting group is trimethylsilyl, addition of a mild aqueous acid solution, such as acetic acid, to the same solution as is employed on step (f) effects removal. Thus there is no need to isolate the compound of formula XI before proceeding to step (g).

Step (h) of these processes involves the removal of the trimethylsilylethyl protected carboxy group at position 3 of the compounds of formula XII to afford the tautomeric compounds having formulas XIII(a) and XIII(b) which exist in equilibrium. The reaction of step (h) is typically conducted in a suitable organic solvent such as tetrahydrofuran, ethyl ether or dioxane at temperatures ranging from about 10° C.–45° C., with room temperature (about 25° C.) being preferred. One functional equivalent of fluoride ion is added so that only the trimethylsilylethyl protected carboxy group is removed. Typically, tetrabutylammonium fluoride is utilized as a source of fluoride ion, although any equivalent source of fluoride ion may be similarly utilized. When tetrabutylammonium fluoride is employed, a stoichiometric excess may be employed so long as only one functional equivalent is employed. Whereas tetrabutylammonium fluoride dissociates slowly in these solutions and as the removal of the allyl protecting group is much slower than removal of the trimethylsilylethyl protected carboxy group, an excess (2 eq) of tetrabutylammonium fluoride results in only one functional equivalent being employed in this reaction step. Isolation of the product at this stage affords the compound of formulas XIII(a) and XIII(b) which may be utilized for further synthesis of penems.

Step (i) of this process involves the reaction of the compound of formulas XIII(a) and XIII(b) with a compound of the formula R-Z wherein R is as hereinabove defined and Z is a leaving group to form a compound of formula XIV. Typically, this reaction step (h) is a continuation of step (g), and is conducted without isolation of the compound of formulas XII(a) and XII(b). Thus, under such circumstances, the solvents utilized in steps (g) and (h) are necessarily the same. When a compound of formulas XII(a) and XII(b) is isolated, the solvents and temperatures suitable for step (h) can be different from those of step (g) but preferably are the same.

Alternatively, step (i) may be conducted by addition of fluoroloweralkyl trifluoromethyl sulfonate (i.e.,

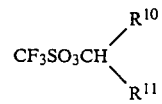

wherein $R^{10}$ and $R^{11}$ are as hereinabove defined) to XIII(a) and XIII(b). The reaction is typically conducted in a suitable organic solvent such as tetrahydrofuran and the like. An essentially equimolar amount of an acid acceptor, such as carbonate, is added to the system to facilitate the reaction. Typically, the reaction is conducted from about −5° to 30° C. and is generally complete from within 1 to 24 hours.

Step (j) of these processes involves the removal of the allyl protecting group on the 3-carboxyl to form a compound of formula I. Removal is effected by the addition of a compound of formula XV to a solution containing palladium (zero) and an alkali alkyl carboxylate, or aqueous carbonate. This step is described by McCombie in U.S. Pat. No. 4,314,942 which is incorporated herein byreference. Most preferably, under these conditions, step (j) procedes with the removal of the allyl protecting group and the formation of the alkali salt of the penem (Formula I) in situ.

Preferably, however, the compound of formulas XIII(a) and XIII(b) are prepared according to process C.

In a highly preferred embodiment of process C of the present invention, the intermediates formed in some of the reaction steps are not isolated but remain in the reaction vessel and are treated according to the next reaction step. This facilitates the process to a very great extent, since several steps can be carried out in the same solvent, without regard to separation of the desired product.

For instance, in the preferred embodiment of process C, the α-substituted allyl acetate of formula XVII is added to the azetidione of formula XVI to form the intermediate of formula XVII.

Again, in the preferred embodiment, the intermediate of formula XVII is utilized directly in steps (b), (c) and (d) without isolation. Thus, steps (b), (c) and (d) are conducted sequentially.

Likewise steps (e) and (f) are conducted sequentially without the necessity of isolating the intermediate.

Step (a) of process C involves the reaction of an azetidione of formula XVI at 15°–30° C. in the presence of an acid acceptor with an α-substituted allyl acetate of formula XVII

wherein W is a leaving group, to form the compound of formula XVIII. Preferred W leaving groups include tosyl, mesyl, chloro, bromo, iodo, and trifluoromethanesulfonyl. Particularly preferred W leaving groups include iodide or bromide.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) of this process involves the conversion of the compound of formula XVIII to the corresponding salt of formula XIX. Step (c) of this process involves the protection of the 6-hydroxy substitutent to form the compound of formula XX with the preferred protecting group being trimethylsilyl whereas step (d) of the process is that wherein the metal salt of formula XX is then converted to a compound of formula XXI by addition of a thiocarbonyl reagent of formula X which has the following structure

wherein Y is a leaving group. Typical of such leaving groups are chloro, bromo, iodo imidazolyl. For the purposes of this process, 1,1'-thiocarbonyldiimadazole is preferred due to its crystalline nature and ease of use. Steps (b), (c) and (d) of process C are conducted as described for steps (d), (e) and (f) of processes A and B described hereinabove.

Step (e) of this process involves the cyclization of the compound of formula XXI into the thione of formulas XXII(a) and XXII(b). The reaction is typically conducted in an anhydrous inert organic solvent such as tetrahydrofuran and the like. An essentially equimolar amount of a strong base such as lithium diisopropyl amide (LDA), lithium di-(trimethylsilyl)amine and the like is added to the system to effect cyclization. Typically, the reaction is conducted at from −50° to −100°

C. and preferably at −70° C. and is generally complete from within 5 minutes to 24 hours.

Step (f) of this process involves the removal of the 6-hydroxy protecting group in the compound of formulas XXII(a) and XXII(b) to form the compound of formulas XIII(a) and XIII(b). This step is accomplished as described hereinabove for step (g) of process A and B.

The following preparations, examples and illustrations describe in detail the processes of the present invention, methods for their preparation of the starting material and illustrations of the use of the intermediates produced by the instant process. Throughout these preparations, examples and illustrations, "NMR" denotes nuclear magnetic resonance spectra; "rotation" denotes optical rotation of the compounds in a suitable solvent; "MS" denotes mass spectra; UV denotes ultraviolet spectra; and "IR" denotes infrared spectra. Chromatography is preformed on silica gel unless otherwise noted. The term "room temperature" refers to about 18°–25° C.. It will be apparent to those skilled in the art that many modifications, both of materials and methods, may be practiced without departing from the purpose and intent of this invention.

In the following Examples, process A is illustrated by Examples 3, 5 and 6, process B is illustrated by Example 3 and process C is illustrated by Example 4.

PREPARATION OF STARTING MATERIALS

EXAMPLE 1

Preparation of (3S,4R)-3-(1-trichloroethoxycarbonyloxyethyl)-4-triphenylmethylthioazetidin-2-one Add to a 250 ml flask 7.8 gm (0.0223 moles) of 3-(1-trichloroethoxycarbonyloxyethyl)-4-acetoxyazetidino-2-one, 220 ml acetonitrile, 2.6 gms (0.252 moles) cesium carbonate, and 5.2 gm (0.0188 moles) triphenylmethanethiol(tritylthiol). After stirring for 5 hours, an additional 1.0 gm (0.0036 moles) triphenylmethanethiol is added and the mixture is stirred for another one-half hour. After overnight refrigeration, the solids are removed by filtration and the solvents by evaporation under vacuum. The crude reaction product is chromatographed on coarse silica gel eluting with methylene chloride changing to 10% and 20% ethyl acetate/methylene chloride to afford 7.89 grams (3S,4R)-3-(1-trichloroethoxycarbonyloxyethyl)-4-(triphenylmethylthio)azetidin-2-one with spectra as follows:

NMR:=7.7–7.1, 16H; 5.05, 1H,; 4.85,2H,q (J=18 Hz); 4.45, 1H, d (J=1.5 Hz); 3.3, 1H, dd (J=1.5, 9 Hz); 1.5, 3H, d (J=6 Hz)

EXAMPLE 2

Preparation of Allyl trimethylsilylethylketomalonate

Add to a 500 ml flask 25 gm ketomalomic acid 1½ H₂O, 250 mg p-toluene sulfonic aid, 58 gm allyl alcohol, and 200 ml benzene. Reflux with a Dean Stark tube for 6½ hours. Remove excess allyl alcohol and benzene by evaoporation under vacuum. Wash the residue with H₂O, then distill at 2 mmHg and collect diallyl ketomalonate as a yellow oil, b.p. 89°–92° C., yield 25 gm. Add 25 gm diallyl ketomalonate to 14.9 gm of (CH₃)₃SiCH₂CH₂OH, then add ½ ml of 1,5-diazabicyclo[4.3.0]non-5-ene (DBN). After 24 hours, wash the resultant mixture with cold 10% phosphoric acid, then with water. Dry the resultant product and distill at 0.4 mmHg to obtain allyl trimethylsilylethylketo malonate, b.p. 91°–100° C., yield 12 gm.

NMR:=0.05, (9H, S); 1.05, (2H, T, J=9 HZ); 4.35, (2H, T, 9 HZ); 4.70, (2H, D, J=6 Hz); 5.25, (2H, M); 5.80, (1H, M)

EXAMPLE 3
Preparation of (5R,6S,8R)-allyl-2-thiol-6-(1-hydroxyethyl)penem-3-carboxylate (A) Preparation of (3S,4R)-1-[1-hydroxy-1-allyloxycarbonyl-1-trimethylsilylethoxycarbonylmethyl]-3-[1-(2,2,2)-trichloroethoxycarbonyloxyethyl)]-4-triphenylmethylthio)azetidin-2-one Add 100 mg of (3S,4R)-3-[1-(2,2,2)-trichloroethoxycarbonyloxyethyl]-4-(triphenylmethylthio)-azetidin-2-one (prepared as described in Example 1 above) and 0.2 ml of dimethylformamide to a dry vial. Add 45 mg of allyl trimethylsilylethylketomalonate (prepared as described in Example 2 above), 0.0014 ml of pyridine and 0.0014 ml of triethylamine to the system. After standing at room temperature for 50 minutes, remove the solvent by stripping to give the title product.

(B) Preparation of (3S,4R)-1-[1-allyloxycarbonyl-1-chloro-1-trimethylsilylethoxycarbonylmethyl]-3-[1-(2,2,2)-trichloroethoxycarbonyloxyethyl]-4-(triphenylmethylthio)azetidin-2-one Add 4.26 gm of (3S,4R)-1-[1-hydroxy-1-alloxycarbonyl-1-trimethylsilylethoxycarbonylmethyl]-3-[1-(2,2,2-trichloroethoxycarbonyloxyethyl)]-4-triphenylmethylthio)azetidin-2-one to a solution of 10 ml of methylene chloride, 2 ml pyridine and 1 gm of calcium carbonate. Cool the system to 0°–5° C. by placing the system in an ice bath. After cooling, slowly add 1.5 ml of thionyl chloride. After 25 minutes, the reaction is complete. Wash the reaction mixture with sodium bicarbonate solution of pH less than 8 and remove the solvent by stripping. Chromatograph the residue on silica gel using methlene chloride as the eluant to afford 3.48 gm of the title compound.

(C) Preparation of (3S,4R)-1-[1-allyloxycarbonyl-1-trimethylsilylethoxycarbonylmethyl]-3-(1-hydroxyethyl)4-(triphenylmethylthio)azetidin-2-one Dissolve 3.48 gm of (3S,4R)-1-[1-allyloxycarbonyl-1-chloro-1-trimethylsilylethoxycarbonylmethyl]-3-[1-(2,2,2)-trichloroethoxycarbonyloxyethyl]-4-(triphenylmethylthio)azetidin-2-one in 50 ml of tetrahydrofuran. To the system add 15 ml of water and 8 gm of zinc dust. Place the system in an ice bath and add 16 gm of ammonium chloride in portions over 1 hour. Stir the solution at 0°–5° C. for an additional 2 hours and then add 4 ml of gl. acetic acid and portionwise, an additional 6 gms of zinc dust. Continue the reaction for an additional 1 hour, filter and remove the solvent by stripping. Dissolve the crude product in methylene chloride and wash the organic solution with water. Purify the crude product by column chromatography on silica gel using as eluant 1% ethylacetate (methylene chloride changing to 25% ethylacetate) to afford the 1.64 gm of title compound.

NMR:=0.05, (5, 9H); 1.05, (m, 2H); 1.15, (D, 3H, J=6); 2.2, (5, 1H); 3.38, (DD, 1H); 3.7, (m); 4.2, (m); 4.5, (m); 5.2, (m, 2H); 5.8, (m, 1H).

(D) Preparation of Silver (3S,4R)-3-(1-hydroxyethyl)-1-allyloxycarbonyl-1-trimethylsilylethoxycarbonylmethylazetidin-2-one-4-thiolate To a 50 ml flask equipped with a nitrogen atmosphere add 5 ml of methanol and 1 gm (0.00158 moles) of (3S,4R)-1-[1-alloxycarbonyl-1-trimethylsilylethoxycarbonylmethyl]-3-(1-hydroxyethyl)-4-triphenylmethylthioazetidin-2-one. Cool the solution to about 0° C. and then add 0.14 ml of pyridine and 1.74 ml of methanol containing 294 mg (0.00173 moles) of silver nitrate. Stir the system at about 0° C. for 1 hour and then allow the system to warm to room temperature. After 2 hours of stirring at room temperature, add an additional 0.2 ml of methanol containing 34 mg of silver nitrate (0.0002 moles) to the system and continue the reaction for an additional 1 hour. Stop the reaction and remove the methanol by stripping. Dissolve the residue in methylene chloride and wash the organic solution twice with water, then with brine. Dry the organic solution over anhydrous sodium sulfate, filter and remove the methylene chloride by stripping to give the title compound.

(E) Preparation of Silver (3S,4R)-3-(1-trimethylsilyloxyethyl)-1-allyloxycarbonyl-1-trimethylsilylethoxycarbonylmethylazetidin-2-one-4-thiolate Dissolve the entire amount of silver (3S,4R)-3-(1-hydroxyethyl)-1-allyloxycarbonyl-1-trimethylsilylethoxycarbonylmethylazetidin-2-one-4-thiolate obtained from step (d) above in 10 ml of anhydrous methylene chloride. Add 0.783 ml (0.00316 moles) of bis trimethylsilyl acetamide to the system. Stir the system at room temperature for 15 minutes to yield the title compound.

(F) Preparation of (5R,6S,8R)-2-thiocarbonyl-3-allyloxycarbonyl-3-trimethylsilylethoxycarbonyl-6-(1-trimethylsilyloxyethyl)penam After the completion of step (e) and to the same solution, add 619 mg (0.00316 moles) of 90% thiocarbonyl diimidazole to the system. Stir the system at room temperature for 20 hours and then filter the solution. Remove the methylene chloride by stripping. Chromatograph the crude product on silica gel eluting with 30% cyclohexane/methylene chloride changing to methylene chloride to afford 704 mg of the title compound.

NMR:=6.2–5.6, m, 1H; 5.65, d (J=1.5 Hz), 1H; 5.5–5.1, (m), 2H; 4.7, d (J=5.5 Hz), 2H; 4.5–4.1, m, 3H; 3.62, d, d (J=1.5, 4 Hz), 1H; 1.28, d (J=6 Hz), 3H; 1.2–0.85, m, 2H; 0.2–0, m, 18H.

(G) Preparation of (5R,6S,8R)-2-thiocarbonyl-3-allyloxycarbonyl-3-trimethylsilylethoxycarbonyl-6-(1-hydroxyethyl)penam To a 25 ml flask add 100 mg of (5R,6S,8R)-2-thiocarbonyl-3-allyloxycarbonyl-3-trimethylsilylethoxycarbonyl-6-(1-trimethylsilyloxyethyl)penam, 1 ml of tetrahydrofuran 0.05 ml of water and 0.05 ml of acetic acid. Stir the system at room temperature for 12 hours. Add ethyl acetate to the solution and was the organic phase with sodium bicarbonate solution, water and then brine. Dry the organic phase over anhydrous sodium sulfate, filter and remove the solvent by stripping to give the title compound.

NMR;=6.15-5.6, m, 1H; 5.69, d(J-2 Hz), 1H; 5.55-5.12, m, 2H; 4.8-4.6, M, 2H; 4.5-4.0, m, 3H; 3.67, d, d (J=2, 7 Hz), 1H; 2.8-2.3, m, 1H; 1.37, d (J=6. Hz), 3H; 1.2-0.8, m, 2H; 0.3-0, m, 9H.

(H) Preparation of (5R,6S,8R)Allyl-2-thiol-6-(1-hydroxyethyl)penem-3-carboxylate To 7.7 mg of (5R,6S,8R)-2-thiocarbonyl-3-allyloxycarbonyl-3-trimethylsilylethoxycarbonyl-6-(1-hydroxyethyl)penam in 1 ml of tetrahydrofuran slowly add at room temperature 2 equivalents of tetrabutylammonium fluoride in 40 ml of tetrohydrofuran. Thin layer chromatography (silica gel, 10% ethylacetate/methylene chloride) shows the immediate presence of the monodeprotected decarboxylated compound (5R,6S,8R)allyl-2-thiol-6-(1-hydroxyethyl)penem-3-carboxylate, which exists in equilibrium with (5R,6S,8R)-allyl-2-thiocarbonyl-6-(1-hydroxyethyl)penam-3-carboxylate NMR:=d 5.85, d (J=1 Hz), 1H; 5.8, m, 1H; 5.25, 5, 1H; 5.4-5.1, m, 2H; 4.7, 2H; 4.25, M, 1H; 3.65, d, d (J=1, 1 Hz), 1H; 2.1, 1H; 1.35, d (J=7 Hz) 3H.

EXAMPLE 4

Preparation of Allyl(5R,6S,8R)-2-thiol-6-(1-hydroxyethyl)penem-3-carboxylate and Allyl(5R,6S,8R)-2-thiocarbonyl-6-(1-hydroxyethyl)penem-3-carboxylate

(A) Preparation of (3S,4R)-1-(allyloxycarbonylmethyl)-3-(1-hydroxyethyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of α-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid NMR:=8.4, 1H, s; 7.65, 1H, d(J=1 Hz); 7.05, 1H (dJ=1 Hz); 5.95, 1H, d (J=2 Hz); 5.8, 1H, m; 5.45-5.1, 2H, m; 4.3, 1H, m; 4.1, 2H, Q(J=16 Hz); 3.5, d d (J=2,6); 1.35; 3H, d (J=6 Hz).

(B) Preparation of Silver (3S,4R)-3-(1-hydroxyethyl)-1-allyloxycarbonylmethylazetidin-2-one-4-thiolate To a 50 ml flask equipped with a nitrogen atmosphere add 10 ml of methanol and 460 mg of (3S,4R)-1-(allyloxycarbonylmethyl)-3-(1-hydroxyethyl)-4-(triphenylmethylthio)azetidin-2-one. To this system add 160 mg silver nitrate and 0.15 ml of pyridine. Stir the system at 20° C. for 1 hour. Stop the reaction and remove the methanol by stripping to give the title compound.

(C) Preparation of Silver (3S,4R)-3-(1-trimethylsilyloxyethyl)-1-allyloxycarbonylmethylazetidin-2-one-4-thiolate Add the entire amount of Silver (3S,4R)-3-(1-hydroxyethyl)-1-allyloxycarbonylmethylazetidin-2-one-4-thiolate produced in step (b) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethylsilyloxyethyl)-4-(1'-imidazolylthiocarbonylthio)azetidin-2-one After completion of step (c) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

(E) Preparation of (5R,6S,8R) allyl-2-thiol-6-(1-trimethylsilyloxyethyl)penem-3-carboxylate and (5R,6S,8R)allyl-2-thiocarbonyl-6-(1-trimethylsilyloxyethyl)penam-3-carboxylate Add 170 mg of (3S,4R)-1-(allyloxycarbonylmethyl)-3-(1-trimethylsilyloxyethyl)-4-(1'-imidazolylthiocarbonylthio)azetidin-2-one to 40 ml of anhydrous tetrahydrofuran under a nitrogen atmosphere. Cool the system to −78° C. and then add 0.6 ml of 1M lithium di(trimethylsilyl)amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R)Allyl-2-thiol-6-(1-hydroxyethyl)penem-3-carboxylate and (5R,6S,8R)Allyl-2-thiocarbonyl-6-(1-hydroxyethyl)penam-3-carboxylate To a 25 ml flask add the entire mixture produced in step (e) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 5

Preparation of (5R,6S,8R) Allyl-2-ethylthio-6-(1-hydroxyethyl)penem-3-carboxylate To the solution of (5R,6S,8R)Allyl-2-thiol-6-(1-hydroxyethyl)penem-3-carboxylate and (5R,6S,8R)Allyl-2-thiocarbonyl-6-(1-hydroxyethyl)penam-3-carboxylate produced in step (b) above add 0.016 ml of ethyl iodide and 16 mg sodium bicarbonate in 0.5 ml water. Stir the system at room temperature for 15 minutes. 25 ml of ethyl acetate is added to the system. Wash the organic solution with water, dry the organic phase with anhydrous sodium sulfate, filter and remove the solvent by stripping to yield the title compound.

EXAMPLE 6

Preparation of (5R,6S,8R) Allyl-2-(2',2',2'-trifluoroethyl)-6-(1-hydroxyethyl)-penem-3-carboxylate 1. Dissolve 0.735 ml pyridine in 25 ml dry toluene and cool to −20° C. under nitrogen. Add 1.45 ml trifluoromethanesulfonic anhydride followed by 0.703 ml 2,2,2-trifluoroethanol and allow to warm to room temperature. Wash the resultant residue with water, dry with anhydrous sodium sulfate and distill, collecting all fractrions with a b.p less than 100° to obtain trifluoromethyl 2,2,2-trifluoroethylsulfurate.

2. Add (5R,6S,8R)allyl-2-thiol-6-(1-hydroxyethyl)-penem-3-carboxylate and (5R,6S,8R) allyl-2-thiocarbonyl-6-(1-hydroxyethyl)penam-3-carboxylate (the product produced by the deprotection of 628 mg of (5R,6S,8R)-2-thiocarbonyl-3-allyloxycarbonyl-3-trimethylsilylethoxycarbonyl-6-(1-hydroxyethyl)penam with 2 equivalents of tetrabutylammonium fluoride) to 3 ml of tetrahydrofuran and 5 ml of trifluoromethyl 2,2,2-trifluoroethylsulfonate. Add 1 equivalent of potassium carbonate (powder) to the system. Continue the reaction at room temperature for 1½ hours and then store the solution in the refrigerator overnight. Remove the solution from the refrigerator and stir at room temperature for 1 hour. Filter the solution and wash with methylene chloride/2% phosphoric acid. Remove the solvent by evaporation. Dissolve the residue in warm 1:1 chloroform:petroleum ether and cool. The product crystallizes from solution to yield 168 mg of the title compound.

(5R,6S,8R)allyl 2-substituted thio-6-(1-hydroxyethyl)penem-3-carboxylates are readily converted to their corresponding alkali salts as described by McCombie in U.S. Pat. No. 4,314,942.

By following the procedures outlined in Examples 3 and 4 above and employing the method described in U.S. Pat. No. 4,314,942, the following compounds of this invention may be prepared:

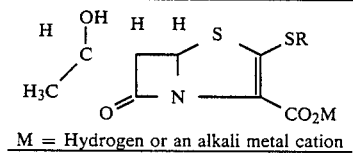

M = Hydrogen or an alkali metal cation

| R | R | R |
|---|---|---|
| —CH$_2$CH$_3$ | —CH$_2$CN | ![N,O,S ring]—NH$_2$ |
| —CH$_2$CH$_2$CH$_3$ | —CH$_2$C(O)CH$_3$ | |
| —CH$_2$CH$_2$F | CH$_2$CO$_2$CH$_3$ | ![N,O,S ring]—NO$_2$ |
| —CH$_2$CH$_2$OH | —CH$_2$C(O)NH$_2$ | |
| —CH$_2$CH$_2$NH$_2$ | —CH$_2$C(O)NHCH$_3$ | —CH$_2$C(=NOH)—C(O)C(O)OC$_2$H$_5$ |
| —CH$_2$CH$_2$OCH$_3$ | —CH$_2$CH$_2$N(CH$_3$)$_2$ | |
| —φ | | |
| —CH$_2$—CH$_2$—S—CH$_3$ | | |
| —CH$_2$φ | —CH$_2$-(N-methylimidazole) | —CH$_2$C(=NH)N(CH$_3$)$_2$ |
| —CH$_2$CH$_2$CH$_2$F | | |
| —CH$_2$CH$_2$Cl | —CH$_2$—CH$_2$—CN | ![N,O,S ring]—NH$_2$ |
| —CH$_2$—OCH$_3$ | | —CH$_2$—C(=NOH)—CH$_3$ |
| —CH$_2$—S—CH$_3$ | —CH$_2$-(thiazole)-NH$_2$ | |
| —CH$_2$—S—CH$_2$CH$_3$ | —CH$_2$—COONa | |

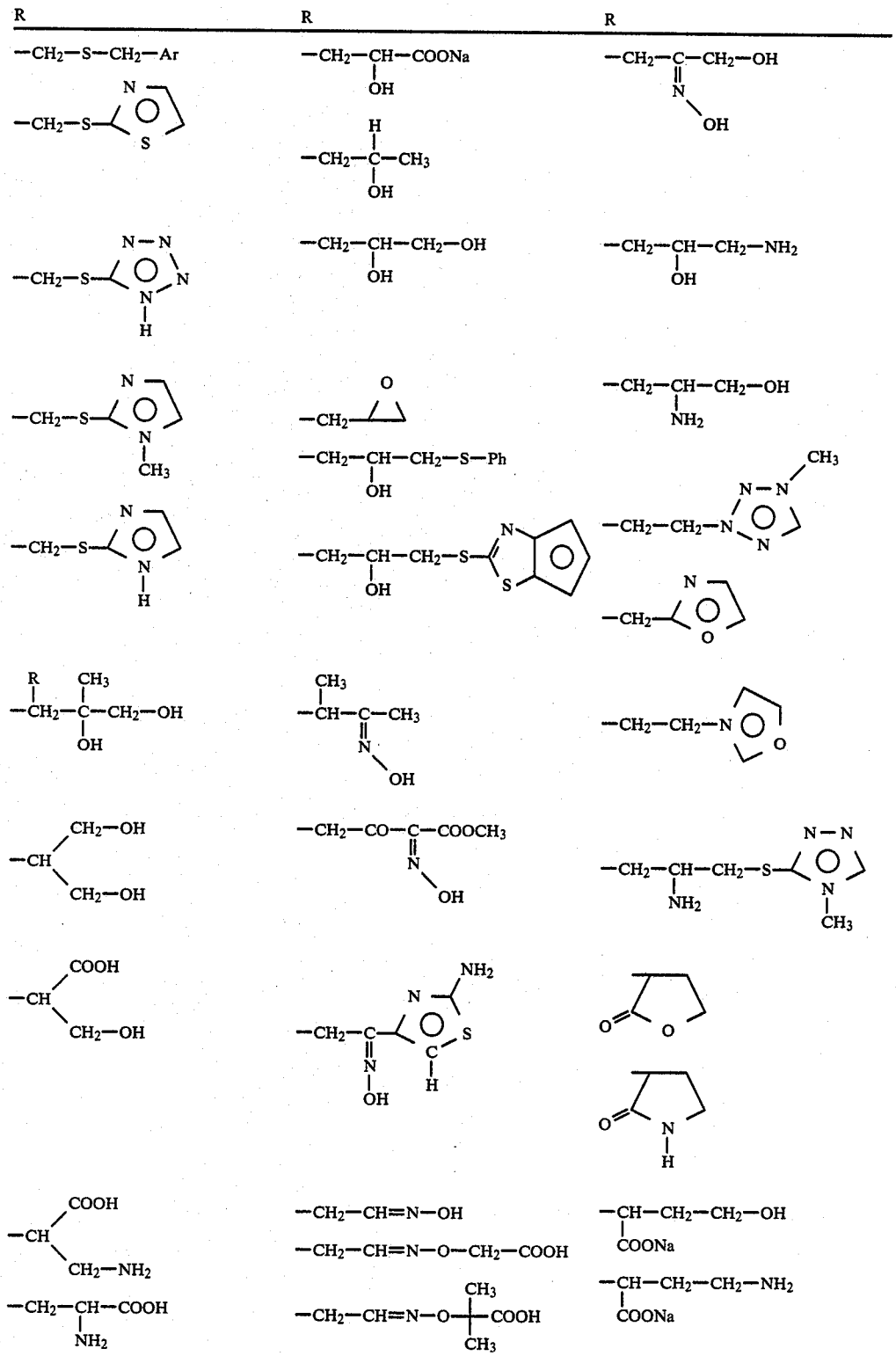

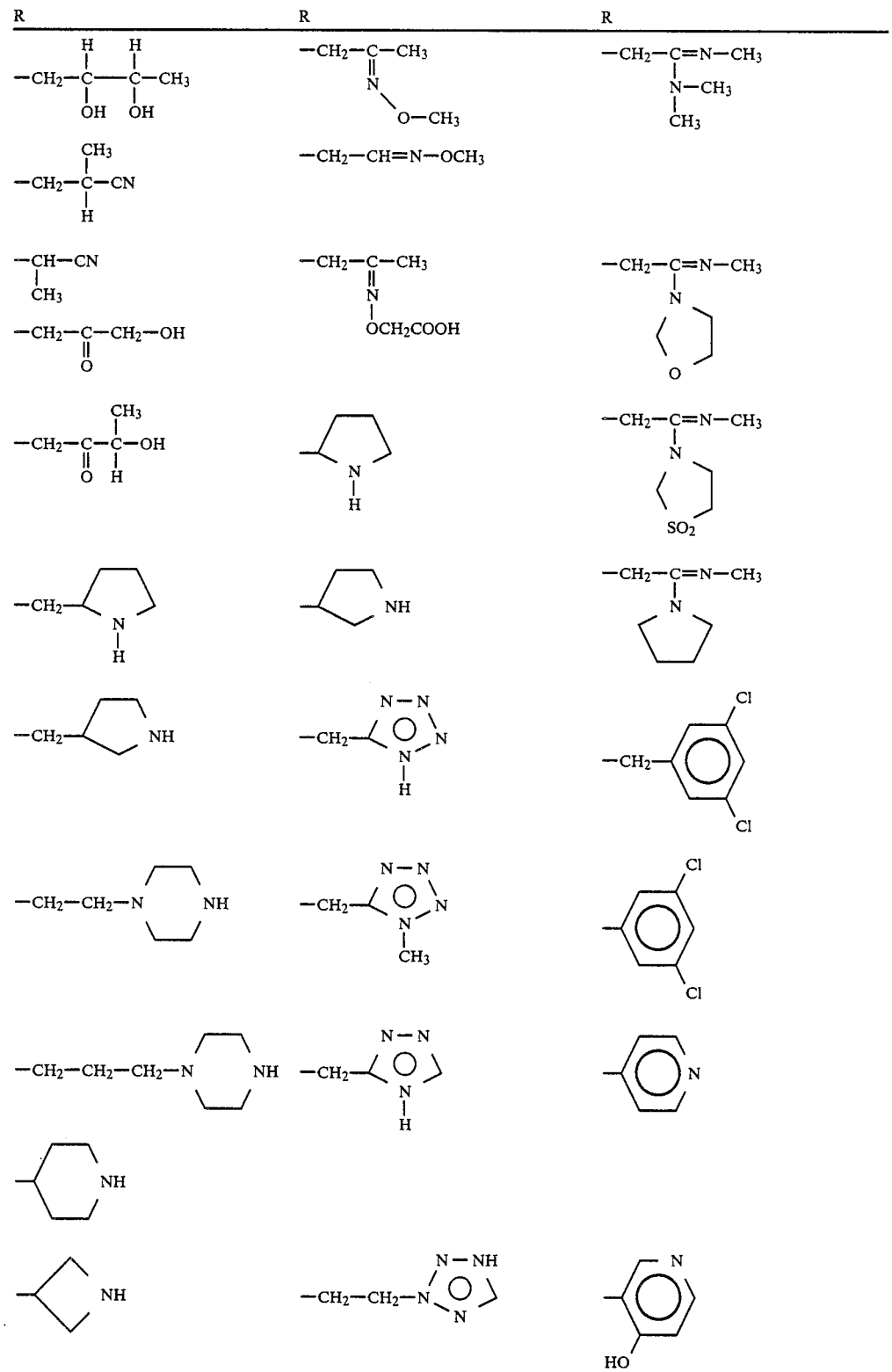

-continued
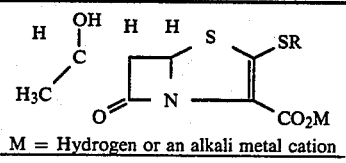
M = Hydrogen or an alkali metal cation
| R | R | R |
|---|---|---|
| 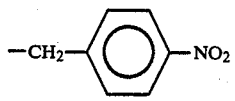 | 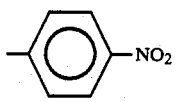 | 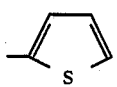 |
| 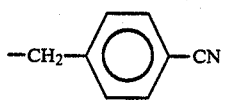 | 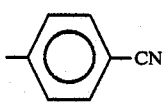 | |
| 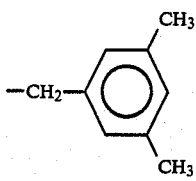 | 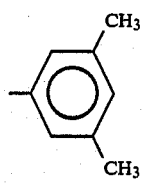 | 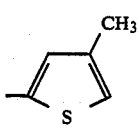 |
| 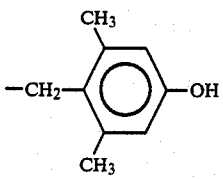 | 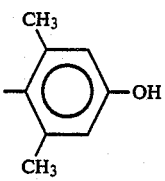 | 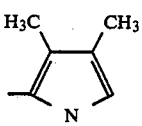 |
| 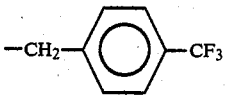 | 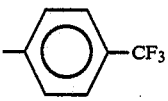 | 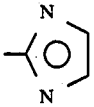 |
| 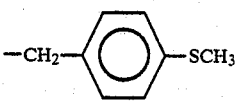 | 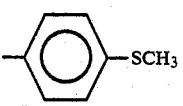 | 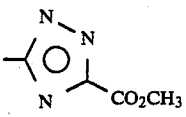 |
| 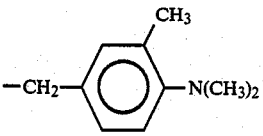 | 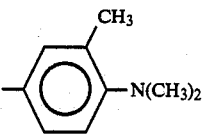 | 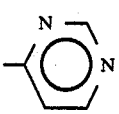 |
| 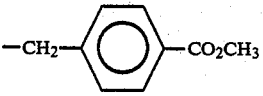 | 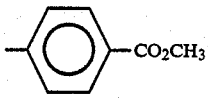 | 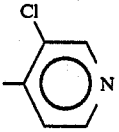 |
| 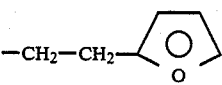 | 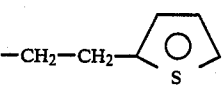 | 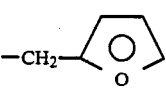 |
| 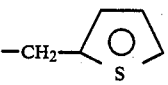 | 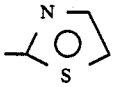 | 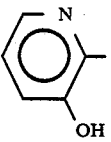 |

-continued

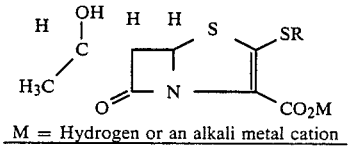

M = Hydrogen or an alkali metal cation

| R | R | R |
|---|---|---|
| 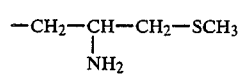 | 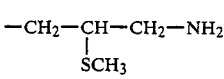 | 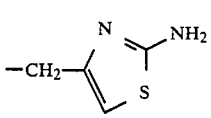 |
| 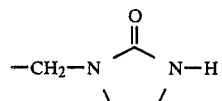 | 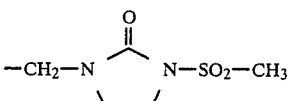 | 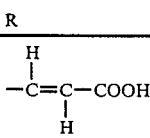 |
| 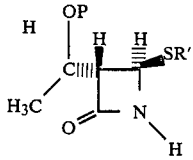 | 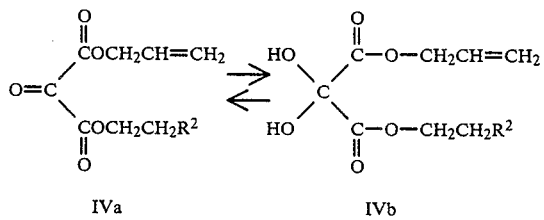 | |

We claim:
1. A process of the production of penems of formula

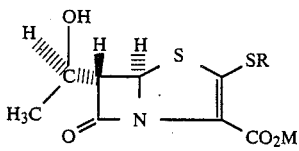

wherein R is a pharmaceutically acceptable organic radical and M is hydrogen or an alkali metal cation; which comprises (a) reaction of an azetidinone of the formula

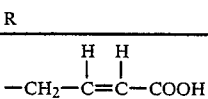   III wherein P is a removable hydroxy protecting group; and $R^1$ is a sulfur protecting group selected from triphenylmethyl, 2-pyranyl, or lower alkyl carbonyl; with a compound of the formula IVa and IVb $H_2O +$

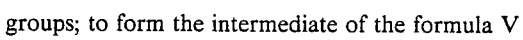

IVa        IVb wherein $R^2$ is trimethylsilyl, t-butyldiphenylsilyl or other equivalently functioning lower alkylsilyl groups; to form the intermediate of the formula V

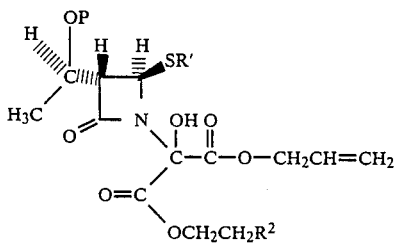   V wherein P, $R^1$ and $R^2$ are hereinabove defined;

(b) treatment of the compound of formula V with a chlorinating agent to form the following compound of formula VI

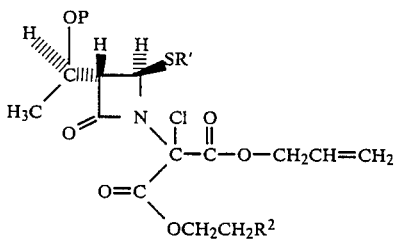   VI wherein P, $R^7$ and $R^2$ are as defined hereinabove;

(c) treatment of the compound of formula VI with elemental zinc to effect removal of the chlorine and the removable hydroxy protecting group, and, if a removable hydroxy protecting group is utilized which is not removable with zinc, subsequent removal of said hydroxy protecting group, producing a compound of formula VII

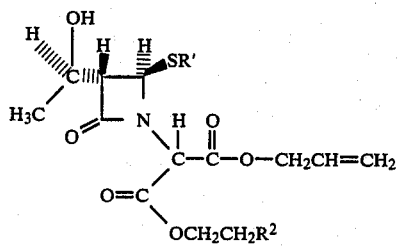

VII wherein $R^7$ and $R^2$ are hereinabove defined;

(d) treatment of the compound of formula VII with a reactive silver, copper or mercury salt to form the compound of formula VIII

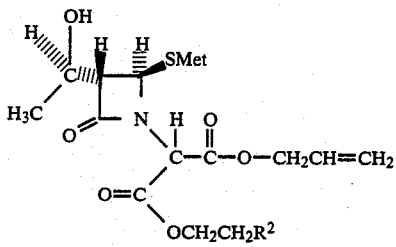

VIII wherein $R^2$ is defined hereinabove and Met is silver, copper or mercury;

(e) treatment of the compound of formula VIII with a hydroxy protecting group to form the compound of formula IX

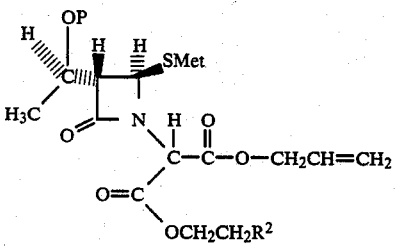

IX wherein $R^2$, P and Met are defined hereinabove;

(f) reaction of the compound of formula IX with a thiocarbonyl compound of formula X

(X)

wherein Y is a leaving group; to form a compound of formula XI

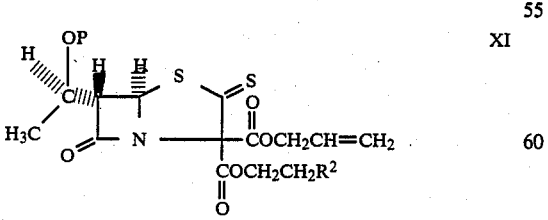

XI wherein P and $R^2$ are as hereinabove defined;

(g) treatment of the compound of formula XI with an aqueous acid solution to form a compound of formula XII

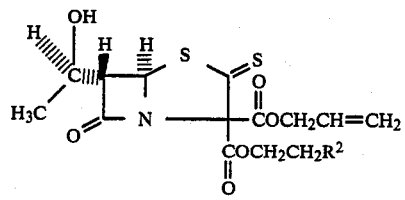

XII (h) treatment of the compound of formula XII with a fluoride ion to form the compound of formula XIIIa which is tautomeric with formula XIIIb

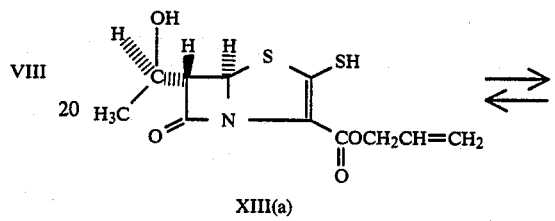

XIII(a)

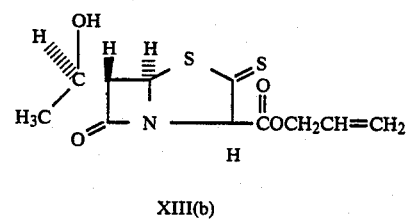

XIII(b)

(i) reaction of the compound of formulas XIII(a) and XIII(b) with either a compound of the formula XIV

(XIV)

wherein R is as defined hereinabove and Z is a leaving group or with

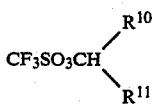

wherein $R^{10}$ and $R^{11}$ are hereinabove defined to form a compound of formula XV

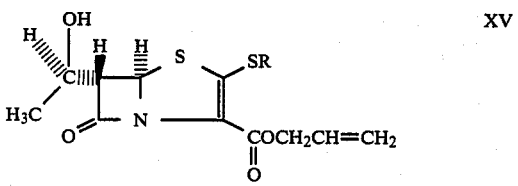

XV wherein R is defined above;

(j) treatment of a compound of formula XV under conditions to remove the allyl protecting group in the presence of an alkali base to form the compounds of formula I

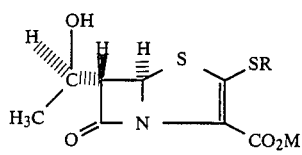

I wherein R and M are as hereinabove defined.

2. A process for the production of penem of the formulas

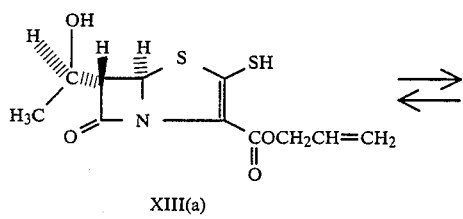

XIII(a)

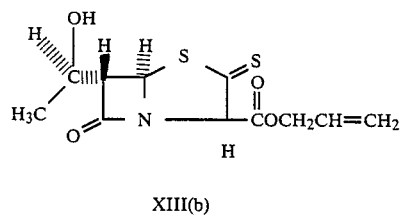

XIII(b)

which comprises (a) reaction of an azetidinone of the formula

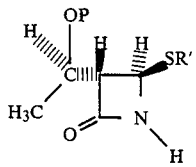

III wherein P is a removable hydroxy protecting group; and $R^1$ is a sulfur protecting group selected from triphenylmethyl, 2-pyranyl, or lower alkyl carbonyl; with a compound of the formula IVa and IVb

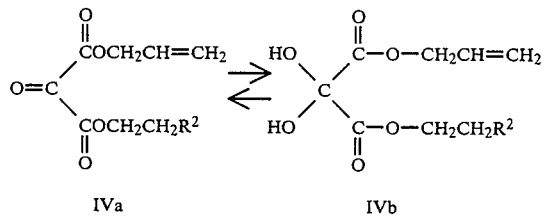

IVa    IVb wherein $R^2$ is trimethylsilyl, t-butyldiphenylsilyl; to form the intermediate of the formula V

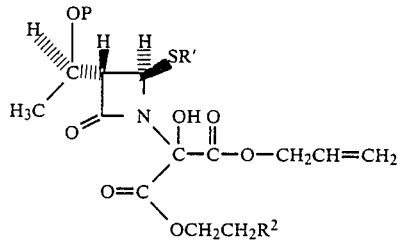

V wherein P, $R^1$ and $R^2$ are hereinabove defined;

(b) treatment of the compound of formula V with a chlorinating agent to form the following compound of formula VI

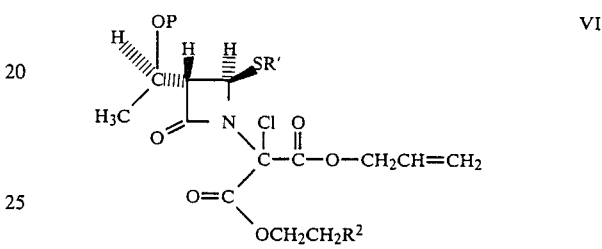

VI wherein P, $R^1$ and $R^2$ are as defined hereinabove;

(c) treatment of the compound of formula VI with elemental zinc to effect removal of the chlorine and the removable hydroxy protecting group, and, if a removable hydroxy protecting group is utilized which is not removable with zinc, subsequent removal of said hydroxy protecting group, producing a compound of formula VII

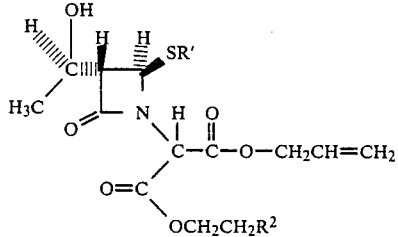

VII wherein $R^7$ and $R^2$ are hereinabove defined;

(d) treatment of the compound of formula VII with a reactive silver, copper or mercury salt to form the compound of formula VIII

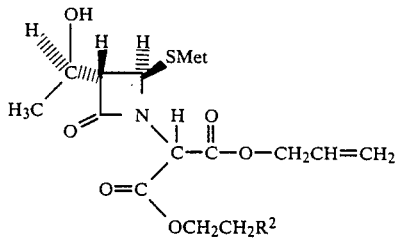

VIII wherein $R^2$ is defined hereinabove and Met is silver, copper or mercury;

(e) treatment of the compound of formula VIII with a hydroxy protecting group to form the compound of formula IX

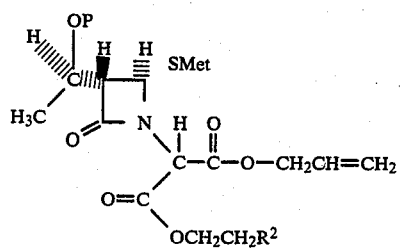

IX wherein $R^2$, P and Met are defined hereinabove;

(f) reaction of the compound of formula IX with a thiocarbonyl compound of formula X $$S=C(-Y)_2 \qquad (X)$$

wherein Y is a leaving group; to form a compound of formula XI

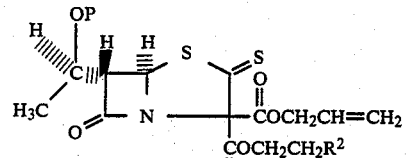

XI wherein P and $R^2$ are as hereinabove defined;

(g) treatment of the compound of formula XI with an aqueous acid solution to form a compound of formula XII

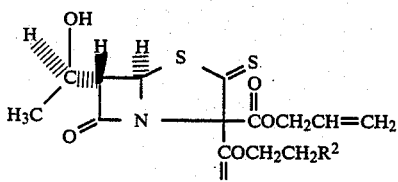

XII (h) treatment of the compound of formula XII with a fluoride ion to form the compound of formula XIIIa which is tautomeric with formula XIIIb

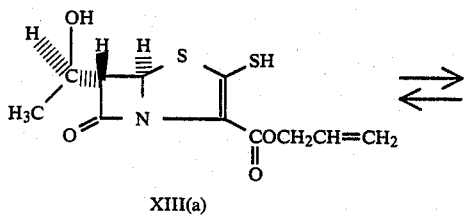

XIII(a)

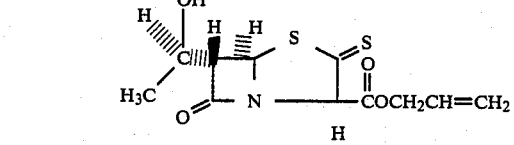

XIII(b)

3. A process for the production of a penem of the formulas

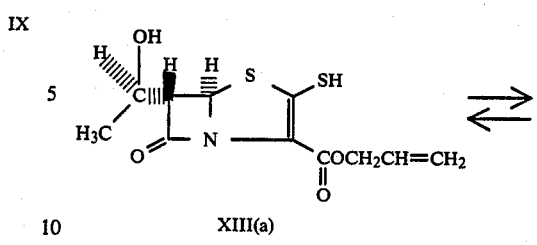

XIII(a)

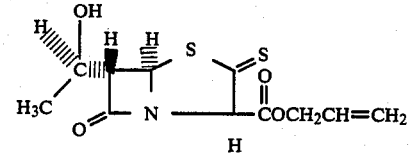

XIII(b)

which comprises (a) reaction of an azetidinone of the formula

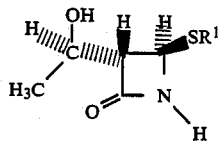

XVI wherein $R^1$ is a sulfur protecting group selected from triphenylmethyl, 2-pyranyl, or lower alkyl carbonyl; with an allyl -substituted acetate of formula XVII $$WCH_2CO_2CH_2CH=CH_2 \qquad XVII$$

wherein W is a leaving group; to form the intermediate of the formula XVIII

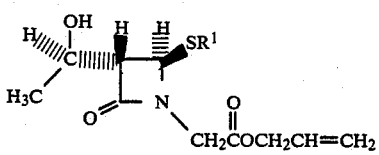

XVIII (b) treatment of the compound of formula XVIII with a reactive silver, copper or mercury salt to form the compound of formula XIX

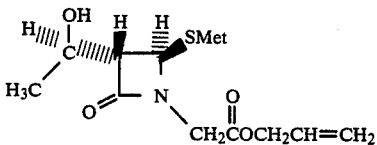

wherein Met is silver, copper or mercury;

(c) treatment of the compound of formula XIX with a hydroxy protecting group to form the compound of formula XX

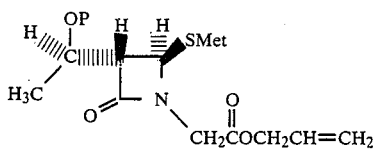 XX wherein P and Met are as hereinabove defined;
(d) reaction of the compound of formula XX with a thiocarbonyl compound of formula X $$S=C(-Y)_2 \qquad (X)$$

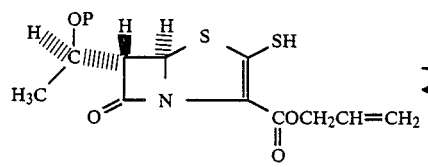

wherein Y is a leaving group to form a compound of formula XXI

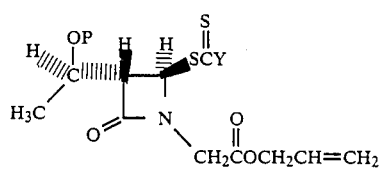 XXI wherein Y and P are as hereinabove defined;
(e) treatment of compound XXI with a nonnucleophilic strong base to form a compound of formula XXII(a) which is tautomeric with formula XXII(b)

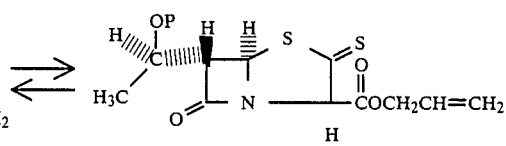

wherein P is as hereinabove defined;
(f) treatment of the compounds of formulas XXII(a) and XXII(b) under conditions which effect removal of the hydroxy protecting group to form the compounds of formula XIII(a) and XIII(b)

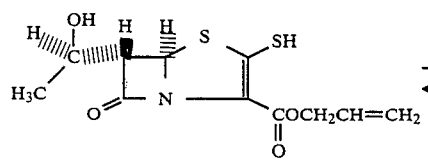 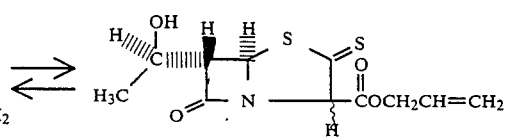

* * * * *